United States Patent [19]
Mahawili

[11] Patent Number: 5,591,220
[45] Date of Patent: Jan. 7, 1997

[54] FLUID REPLACEMENT APPARATUS FOR USE WITH A PORTABLE HEATING AND COOLING SYSTEM

[76] Inventor: Imad Mahawili, 1603 Laraway Lake S.E., Grand Rapids, Mich. 49546

[21] Appl. No.: 452,307

[22] Filed: May 26, 1995

Related U.S. Application Data

[63] Continuation-in-part of Ser. No. 309,360, Sep. 20, 1994, Pat. No. 5,486,207.

[51] Int. Cl.⁶ .................................................. A61F 7/00
[52] U.S. Cl. .................................... 607/104; 607/114
[58] Field of Search ............................ 607/104, 108–112, 607/114

[56] References Cited

U.S. PATENT DOCUMENTS

| | | | |
|---|---|---|---|
| 4,459,468 | 7/1984 | Bailey | 607/104 |
| 5,336,249 | 8/1994 | Mahawili | 607/104 |

*Primary Examiner*—Angela D. Sykes
*Assistant Examiner*—Ryan Carter
*Attorney, Agent, or Firm*—Robert Charles Hill

[57] ABSTRACT

A fluid replacement apparatus for use with a portable body heating and cooling system is provided. The apparatus includes a frame with a support portion configured for supporting a reservoir of the portable body heating and cooling system. A heat exchange mechanism is retained in the frame. The heat exchange mechanism includes a thermostatically controlled receptacle for maintaining fluid circulating through the receptacle at a desired temperature. A cover member covers the reservoir to releasably couple the fluid replacement apparatus to the portable body heating and cooling system. The cover member includes a pump for circulating fluid between the heat exchange mechanism and the reservoir of the portable body heating and cooling system. Return and supply tubes extend between the cover member and the heat exchange mechanism. The supply tube is coupled to the pump land to a receptacle of the heat exchange mechanism for circulating fluid from the reservoir to the receptacle. The return tube is coupled to the receptacle and extends through the cover member for circulating fluid from the receptacle to the reservoir at the desired temperature, for maintaining the temperature of the fluid in the reservoir at the desired temperature.

12 Claims, 2 Drawing Sheets

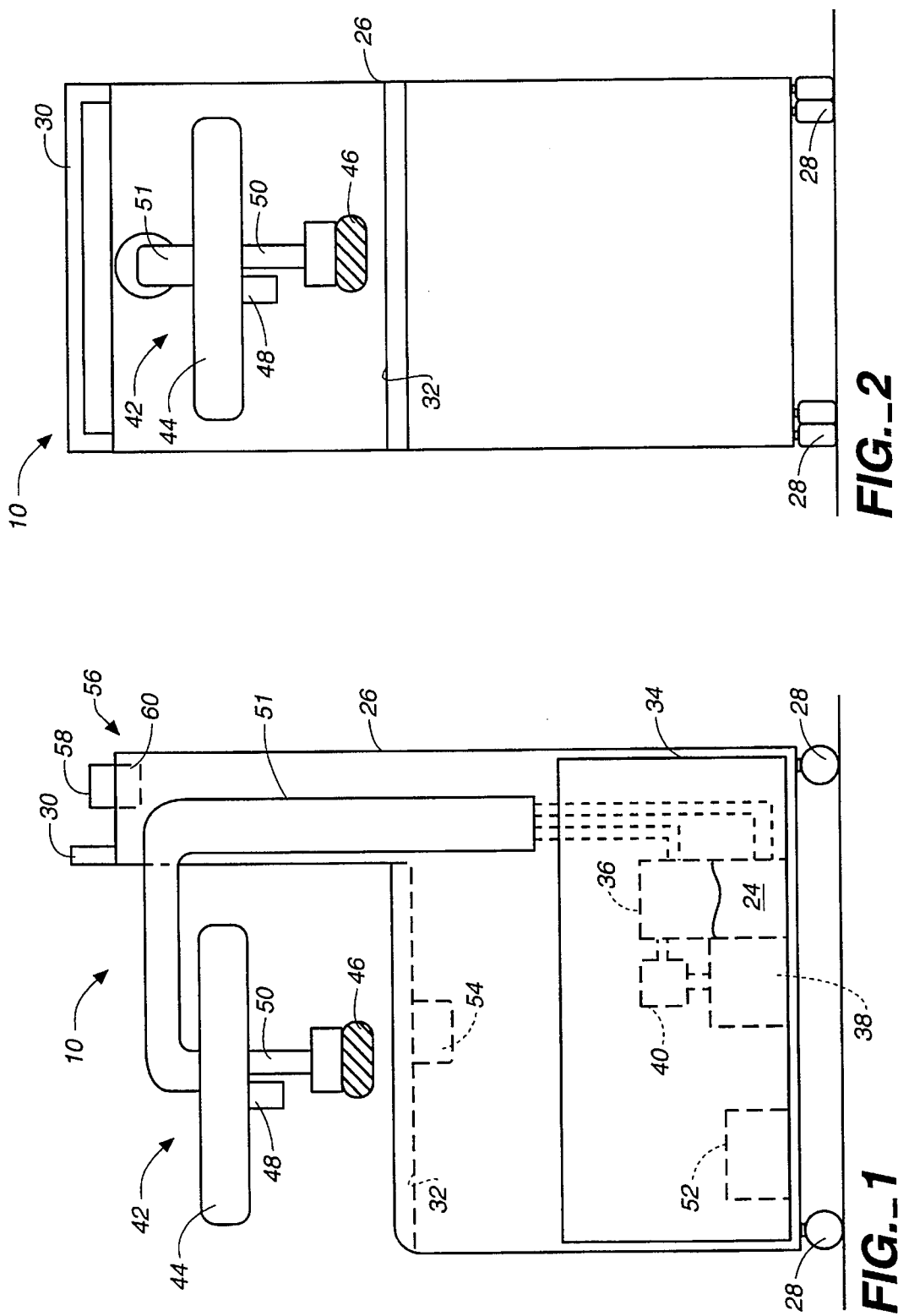

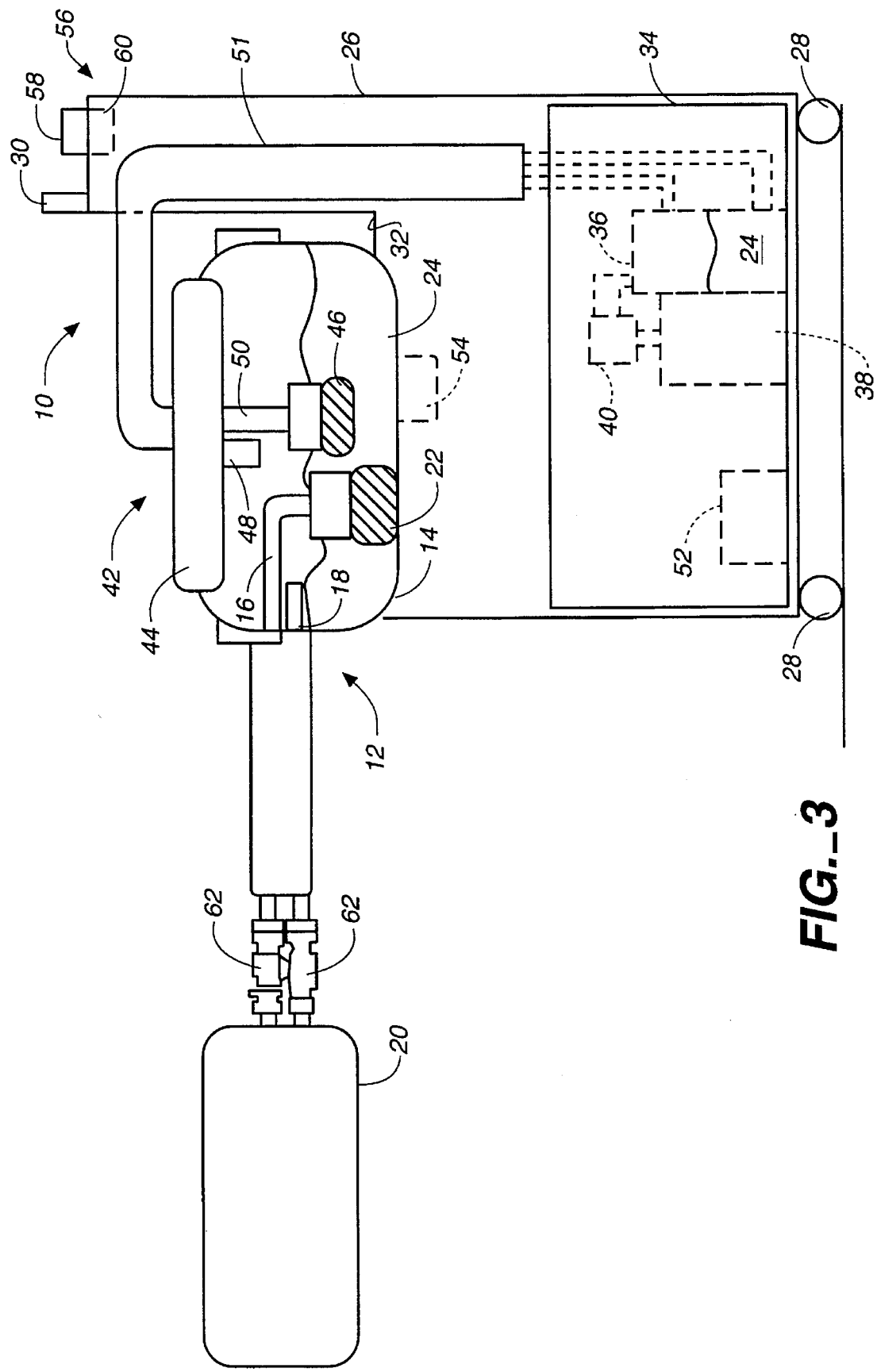
FIG._3

5,591,220

FLUID REPLACEMENT APPARATUS FOR USE WITH A PORTABLE HEATING AND COOLING SYSTEM

BACKGROUND OF THE INVENTION

This is a continuation-in-part of application Ser. No. 08/309,360, filed Sep. 20, 1994, now U.S. Pat. No. 5,486,207, issued Jan. 23, 1996.

1. Field of the Invention

The present invention related generally to systems for heating or cooling selected body portions, and more particularly, to a fluid replacement apparatus for use with a portable body heating or cooling system.

2. Description of Related Art

The use of thermal pads for applying hot or cold therapy to different portions of the body has long been recognized as a desirable treatment for a number of conditions. Such treatment has been found helpful in relieving the pain of injuries and arthritis as well as in treating selected body portions such as joints, muscles, and the like for sprains, excessive exercise, and numerous other conditions.

It is to be noted that the different body portions to be subjected to such treatment include portions of the limbs which can readily be wrapped or encased by a thermal pad as well as substantial, relatively flat portions of the body trunk where the pad must generally be applied in an extended or flat condition.

In treatments of the type summarized above, thermal pads for applying both hot and cold therapy have most commonly relied upon providing a thermal pad which is either hot or cold depending upon the desired treatment. For example, such uses commonly employ heat pads immersed in hot fluid or liquid, electric heat pads, chemical heat pads, cold packs immersed in cold fluid or liquid, and direct application of ice to body portions by means of such a thermal pad. These forms of treatment commonly resulted in hot spots, cold spots, cold burns, uncomfortable ice-body contact, moisture on the selected body parts being treated and usually relatively rapid loss of either the hot or cold condition of the pad. Accordingly, it was also necessary to frequently change the pads or to re-immerse them in either hot or cold fluid or liquid.

Although many of the improved systems still employ pads which are themselves either hot or cold, certain prior art systems have been provided for supplying either hot or cold fluid from a separate source. However, these systems were relatively complex. One such system involved the use of an insulated container filled with either hot or cold fluid and connected with heating/cooling units shaped to conform to particular body portions such as the feet or joints. In these prior art systems, fluid from the separate container was allowed to flow to a cuff by gravity and after a selected period of time, the container could be lowered to permit the fluid to flow from the cuff back into the container.

A portable hearing/cooling system that may be used with the present invention is disclosed in U.S. Pat. No. 5,336,249, issued Aug. 9, 1994, to the inventor of the present invention. The disclosed portable body heating and cooling system includes an insulated reservoir for containing hot or cold fluid. Non-collapsible supply and return tubes couple the reservoir to tubular conduits in a flexible thermal pad. Preferably battery operated and preferably located in the reservoir, a pump is provided for continually circulating fluid from the reservoir, through the tubular conduits, and back to the reservoir.

A disadvantage of the disclosed system, is that while the reservoir is insulated, additional heating or cooling agents may have to be added to the fluid or liquid in the reservoir to maintain the fluid or liquid at a desired temperature. For example, during cold therapy ice may have to be intermittently added to the fluid or liquid in the reservoir, to maintain the fluid or liquid near the desired temperature. Adding ice to the reservoir may cause an unnecessary burden on support staff and ice generating equipment. Additionally, ice may block the tubes coupling the reservoir to the thermal pad, thus restricting circulation of fluid between the pad and reservoir.

Although these prior art systems and devices were found to be generally adequate for their intended purpose, there has been found to remain a need for further improvements in such systems and methods of use for achieving improved treatment.

SUMMARY OF THE INVENTION

Accordingly, it is an object of the present invention to provide a fluid replacement apparatus to operate in combination with a portable body heating and cooling system of the type disclosed in the patent noted above, to the present inventor.

More specifically, it is an object of the present invention to provide a fluid replacement apparatus for use with the portable body heating and cooling system for thermal treatment of selected body pans, that substantially maintains the temperature of fluid or liquid in a reservoir of the portable body heating and cooling system at a desired optimum operating temperature during treatment to a patient.

It is a further object of the present invention to provide a fluid replacement apparatus for use with the portable body heating and cooling system for thermal treatment of selected body parts, that maintains the temperature of chilled fluid in the reservoir of the portable body heating and cooling system at an optimum operating temperature to eliminate the need of addition of ice to the reservoir during treatment to a patient.

These and other objects and advantages of the present invention are achieved by providing a fluid replacement apparatus for use with a portable body heating and cooling system. The apparatus is designed to have a substantially high circulation rate, ranging from approximately 50 to 200 gallons per hour, to ensure rapid equilibration of the circulating fluid to maintain the fluid in the reservoir at the desired optimum operating temperature.

The apparatus includes a frame with a support portion configured to mate to the reservoir of the portable body heating and cooling system for supporting the reservoir.

A heat exchange means is retained in the frame. The heat exchange means includes a thermostatically controlled receptacle for maintaining fluid circulating through the receptacle at a desired temperature. The heat exchange means has a relatively low-power refrigeration unit to maintain fluid circulated through the receptacle at the desired temperature. The refrigeration unit has a thermal power load rating, ranging from substantially 100 to 400 BTU (British Thermal Units). Therefore, in cooling applications, ice does not have to be intermittently added to the reservoir, thus relieving support staff and ice generating equipment.

A cover member replaces a removable cover on the reservoir. The cover member covers the reservoir to releasably couple the fluid replacement apparatus to the portable body heating and cooling system. The cover member includes a pump for circulating fluid between the heat exchange means and the reservoir of the portable body heating and cooling system.

Return and supply robes extend between the cover member and the heat exchange means. The supply robe is coupled to the pump and to the receptacle for circulating fluid from the reservoir to the receptacle. The return robe is coupled to the receptacle and extends through the cover member for circulating fluid from the receptacle to the reservoir at the desired operating temperature, for maintaining the temperature of the fluid in the reservoir at the desired temperature.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, in which:

FIG. 1 is a side elevational, schematic view of a preferred embodiment of a fluid replacement apparatus for use with a portable body heating and cooling system of the present invention;

FIG. 2 is a front elevational, schematic view of the preferred embodiment of the fluid replacement apparatus of the present invention; and FIG. 3 is a side elevational, schematic view, showing the preferred embodiment of the invented fluid replacement apparatus coupled to a portable body heating and cooling system.

DESCRIPTION OF THE PREFERRED EMBODIMENTS

The following description is provided to enable any person skilled in the art to make and use the invention and sets forth the best modes contemplated by the inventor of carrying out his invention various modifications, however, will remain readily apparent to those skilled in the art, since the generic principles of the present invention have been defined herein.

Referring now to the drawing figures, there is shown generally at 10 a fluid replacement apparatus for use with a portable body heating and cooling system shown generally at 12. Referring particularly to FIG. 3 the portable body heating and cooling system 12 includes a reservoir 14, a supply tube 16 and a return tube 18 for interconnection between the reservoir 14 and a thermal pad 20. A pump 22 is provided for continually circulating fluid or liquid 24 between the reservoir 14 and thermal pad 20, which pad 20 may have a single corrugated tube connected to supply and return tubes as disclosed in Ser. No. 08/309,360.

Referring again to the drawing figures, the invented fluid replacement apparatus 10 comprises a body or frame 26 that may be supported by caster wheels 28, for example, for facile transportation of the apparatus 10. A handle 30 may be provided for controlling the apparatus 10 during transportation, such as moving the apparatus 10 to various locations in a hospital (not shown). The frame 26 includes a support shelf 32 configured to support the reservoir 14.

The apparatus 10 includes a heat exchange means shown generally at 34 retained in the frame 26 below the shelf 32. In the preferred embodiment, the heat exchange means 34 includes a receptacle 36 for holding the fluid or liquid 24, a low-power refrigeration unit 38 coupled to the receptacle 36, and a thermostat means 40. The thermostat means 40 thermostatically controls the receptacle 36 for maintaining the fluid 24 circulating through the receptacle 36 at a desired optimum operating temperature. The thermostat means 40 may comprise any suitable commercially available thermostat. The receptacle 36 may be cylindrical for example, and is fabricated using well known thermally conductive materials.

The low-power refrigeration unit 38 comprises a suitable commercially available refrigeration unit having a thermal power load range rating of approximately 100–400 BTU (British Thermal Units). Further, the refrigeration unit 38 is preferably cooled by means other than a fan, such as air cooling, to reduce noise generated by the unit 38. It is to be understood, that alternatively, a suitable heating unit (not shown) may be retained in the heat exchange means 34 and coupled to the receptacle 36. The heating unit would heat fluid 24 circulating through the receptacle 36 to a desired temperature, to provide warm fluid 24 to the reservoir 14.

Coupling 42 means are provided for releasably coupling the invented apparatus 10 to the portable body heating and cooling system 12. The coupling means 42 includes a cover member 44 adapted to replace a removable cover (not shown) of the reservoir 14. The coupling means 42 also includes a pump 46 for circulating fluid 24 between the heat exchange means 34 and reservoir 14. In the preferred embodiment, the pump 46 comprises a suitable 12 VDC pump.

Return and supply tubes 48, 50 extend between the coupling means 42 and the receptacle 36. The supply tube 50 is coupled to the pump 46 and to the receptacle 36 for circulating fluid 24 from the reservoir 14 to the receptacle 36. The return tube 48 is coupled to the receptacle 36 and extends through the cover 44 for circulating fluid 24 from the receptacle 36 to the reservoir 14 at a desired optimum operating temperature, o for maintaining the temperature of the fluid 24 in the reservoir 14 at the desired optimum operating temperature. An appropriate insulative material 51 may be disposed about the tubes 48, 50 to aid with maintaining the temperature of the fluid 24.

A suitable power source 52, such as a 12 VDC battery, for example, is retained in the frame 26 for supplying power to the heat exchange means 34 and to the pump 46. A 12 VDC power outlet 54 may be provided for coupling the power source 52 to the portable body heating and cooling system 12 to supply power to the system 12, when the system 12 is coupled to the apparatus 10.

A solid state control means shown generally at 56 is coupled to the power source 52. The control means 56 includes a switch 58 for activating and deactivating the apparatus 10. The control means 56 may further include a known solid state time delay controller 60 to control the activation and deactivation time periods of the invented apparatus 10 and portable heating and cooling system 12.

In use, the fluid 24 is stored in the reservoir 14. In cold therapy applications, the fluid 24 is initially chilled by adding ice (not shown) to the fluid 24, when the fluid 24 is disposed in the reservoir 14. The fluid 24 quickly reaches a desired optimum operating temperature of approximately 35° Fahrenheit. The thermal pad 20 is positioned on the selected body portion of a patient (not shown) to be treated. Suitable fittings 62 are provided for coupling the reservoir 14 to the thermal pad 20. The heating and cooling system's pump 22 is activated, and the system 12 starts continuously circulating the cold fluid 24 from the reservoir 14, through the thermal pad 20 and back to the reservoir 14. Simultaneously, the apparatus' pump 46 begins continuously pumping to circulate fluid 24 from the reservoir 14 to the receptacle 36 in the heat exchange means 34. The supply and return tubes 50, 48, pump 46, and receptacle 36 are designed to have a substantially high circulation rate, ranging from approximately 50 to 200 gallons per hour, to ensure rapid equilibration of the circulating fluid 24, to maintain the fluid 24 in the reservoir 14 at the desired optimum operating temperature.

The temperature of the cold fluid 24 increases as the fluid 24 circulates through the thermal pad 20 and back to the reservoir 14, due to heat radiated by the body portion being treated and ambient temperature, for example. As the fluid 24 is circulating from the reservoir 14 to the pad 20, the fluid 24 is simultaneously circulating from the reservoir 14 to the receptacle 36. As the reservoir 14 is receiving warmer fluid 24 from the pad 20, the fluid 24 is being drawn from the reservoir 14, by the pump 46, to the receptacle 36, to cool the fluid 24 to the desired operating temperature. Thus, the temperature of the fluid 24 in the reservoir 14 is substantially maintained at the optimum operating temperature, without ice being intermittently added to the reservoir 14, thus relieving support staff and ice generating equipment. Further, since ice is not added to the reservoir 14 during treatment to the selected body portion, blockage of the tubes 16, 18 coupling the reservoir 14 to the thermal pad 20 does not occur, and circulation of fluid 24 therebetween is not restricted.

Thus, there has been described an improved fluid replacement apparatus for use with a portable body heating and cooling system. The invented fluid replacement apparatus maintains fluid in the reservoir at the desired optimum operating temperature during treatment to the selected body portion. The apparatus has a substantially high circulation rate to aid with maintaining fluid in the reservoir at the desired optimum operating temperature. The relatively low-power refrigeration unit maintains the desired temperature of the fluid, so that ice does not have to be intermittently added to the reservoir, thus relieving support staff and ice generating equipment.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A fluid replacement apparatus for use with a portable body heating and cooling system for thermal treatment to selected body portions, said portable body heating and cooling system including a reservoir, interconnection means for connecting the reservoir to a thermal pad, and pump means for continually circulating fluid between the reservoir and the thermal pad, said fluid replacement apparatus comprising:

heat exchange means including a receptacle and means for thermostatically controlling the temperature of fluid in said receptacle to maintain fluid circulating through said receptacle at the desired temperature;

coupling means for releasably coupling the portable body heating and cooling system to said fluid replacement apparatus comprising a support means for supporting the reservoir of said portable body heating and cooling system and cover means for covering said reservoir to couple said fluid replacement apparatus to said portable body heating and cooling system, said coupling means further including said pump means for circulating fluid between said heat exchange means and the reservoir of said portable body heating and cooling system; and connecting means for connecting said coupling means to said heat exchange means, said connecting means enabling said pump means to circulate fluid between said reservoir and said heat exchange means for maintaining fluid in said reservoir at the desired temperature.

2. The apparatus of claim 1 wherein said connecting means comprises return and supply tubes extending between said coupling means and said heat exchange means, said supply tube coupled to said pump means and to said receptacle for circulating fluid from the reservoir to said receptacle, said return tube coupled to said receptacle and extending through said cover means for circulating fluid from said receptacle to said reservoir at the desired temperature for maintaining the temperature of the fluid in the reservoir at the desired temperature.

3. The apparatus of claim 2 wherein said pump means comprises a 12 VDC pump coupled to the supply tube to circulate fluid between said reservoir and said heat exchange means.

4. The of claim 1 further comprising power means for supplying power to said heat exchange means and to said pump means, and control means for controlling said power means.

5. The apparatus of claim 4 further comprising a 12 VDC power outlet for coupling said power means to said portable body heating and cooling system to supply power thereto when said system is coupled to said apparatus.

6. A fluid replacement apparatus for use with a portable body heating and cooling system for thermal treatment to selected body portions, said portable body heating and cooling system including a reservoir, supply and return tubes for interconnection between the reservoir and a thermal pad, and a pump means for continually circulating fluid between the reservoir and the thermal pad, said fluid replacement apparatus comprising:

a frame, said frame including a support portion configured for supporting the reservoir of said portable body heating and cooling system;

a heat exchange means retained in said frame, said heat exchange means including a thermostatically controlled receptacle for maintaining fluid circulating through the receptacle at a desired optimum operating temperature for use by said portable body heating and cooling system;

coupling means for releasably coupling said portable body heating and cooling system to said fluid replacement apparatus, said coupling means including a cover member for covering said reservoir to couple said fluid replacement apparatus to said portable body heating and cooling system, said coupling means further including a pump for circulating fluid between said heat exchange means and the reservoir of said portable body heating and cooling system; and return and supply tubes extending between said coupling means and said heat exchange means, said supply tube coupled to said pump and to said receptacle for circulating fluid from the reservoir to said receptacle, said return tube coupled to said receptacle and extending through said cover member for circulating fluid from said receptacle to said reservoir at the desired operating temperature for maintaining the temperature of the fluid in the reservoir at the operating temperature.

7. The apparatus of claim 6 wherein said heat exchange means includes a low-power refrigeration unit coupled to said receptacle for reducing the temperature of fluid circulated from said reservoir to said receptacle to the desired operating temperature so that fluid circulate from said receptacle to said reservoir is at the operating temperature.

8. The apparatus of claim 7 Wherein said refrigeration unit has a thermal power load rating ranging from substantially 100 to substantially 400 British. Thermal Units.

9. The apparatus of claim 6 wherein said apparatus circulates fluid therethrough at a rate ranging from substantially 50 to substantially 200 gallons per hour.

10. The apparatus of claim 6 wherein said pump comprises a 12 VDC pump coupled to the supply tube to circulate fluid between said reservoir and said receptacle.

11. The apparatus of claim 6 further comprising power means for supplying power to said heat exchange means and to said pump, and solid state control means for controlling said power means.

12. A method for employing a portable body heating and cooling system for thermal treatment, said method comprising the steps of:

storing a cold fluid in a reservoir, said fluid stored in said reservoir at a desired optimum temperature;

arranging a thermal pad in a thermally conductive relationship with a selected body portion to be treated;

coupling the reservoir to the thermal pad;

continuously circulating the cold fluid from the reservoir to the thermal pad, the temperature of the cold fluid increasing as the fluid circulates through said thermal pad;

providing a fluid replacement apparatus, said fluid replacement apparatus including heat exchange means having a receptacle and means for thermostatically controlling the temperature of fluid in said receptacle, for maintaining fluid circulated therethrough at the desired optimum temperature;

releasably coupling said fluid replacement apparatus to said reservoir;

continuously circulating fluid from said reservoir to said heat exchange means for reducing the temperature of fluid from said reservoir to the optimum temperature; and continuously circulating fluid from said heat exchange means to said reservoir for continually providing said reservoir with fluid at the optimum temperature to maintain the temperature of the fluid in the reservoir at the optimum temperature.

* * * * *